(12) United States Patent
Lee et al.

(10) Patent No.: US 10,125,054 B2
(45) Date of Patent: Nov. 13, 2018

(54) APPARATUS AND METHOD FOR IMPROVING ADHESIVE STRENGTH OF DENTAL RESTORATION

(71) Applicants: Chang Taek Lee, Gwangmyeong-Si (KR); Rafael Wonjun Choi, Clarksburg, MD (US)

(72) Inventors: Chang Taek Lee, Gwangmyeong-Si (KR); Rafael Wonjun Choi, Clarksburg, MD (US)

(*) Notice: Subject to any disclaimer, the term of this patent is extended or adjusted under 35 U.S.C. 154(b) by 105 days.

(21) Appl. No.: 15/051,680

(22) Filed: Feb. 24, 2016

(65) Prior Publication Data
US 2017/0135783 A1    May 18, 2017

(30) Foreign Application Priority Data

Nov. 13, 2015 (KR) .................. 10-2015-0159264

(51) Int. Cl.
*C04B 41/91* (2006.01)
*A61C 5/10* (2006.01)
(Continued)

(52) U.S. Cl.
CPC .............. *C04B 41/91* (2013.01); *A61C 5/10* (2013.01); *C04B 35/48* (2013.01);
(Continued)

(58) Field of Classification Search
CPC .................................................... C04B 41/91
(Continued)

(56) References Cited

U.S. PATENT DOCUMENTS

| 2011/0309540 A1* | 12/2011 | Dittmann | F27D 5/0043 264/16 |
| 2013/0177876 A1* | 7/2013 | Homann | A61C 8/0012 433/201.1 |
| 2014/0272799 A1* | 9/2014 | Piascik | A61K 6/0255 433/199.1 |

FOREIGN PATENT DOCUMENTS

| KR | 10-2005-0084293 | 8/2005 |
| KR | 10-2008-0094625 | 10/2008 |
| KR | 10-2013-0138578 | 12/2013 |

OTHER PUBLICATIONS

Korean Office Action dated Feb. 25, 2016 from Korean Patent Application No. 10-2015-0159264, 4 pgs.

* cited by examiner

*Primary Examiner* — Andrew J Bowman
(74) *Attorney, Agent, or Firm* — Ichthus International Law PLLC

(57) ABSTRACT

A method and apparatus for producing a dental restoration with enhanced adhesive or bonding strength are disclosed. The dental restoration comprises a zirconia based crown and a porcelain layer built-up on a top surface of the zirconia based crown. The zirconia based crown is to be bonded to a top of an abutment tooth and has dimensions that are smaller than outer dimensions of the abutment tooth. A first surface of the zirconia based crown is configured to adhere to the abutment tooth and a second surface of the zirconia based crown is configured to receive the porcelain layer built-up. The first surface and the second surface of the zirconia based crown are treated with a surface treatment solution which includes at least nitric acid ($HNO_3$), hydrofluoric acid (HF) and hydrogen peroxide ($H_2O_2$). Further, the zirconia based crown may be treated with an ultrasonic impact treatment in (Continued)

addition to the surface treatment of the zirconia based crown.

11 Claims, 12 Drawing Sheets

(51) Int. Cl.
*C04B 35/48* (2006.01)
*C04B 35/626* (2006.01)
*C04B 35/64* (2006.01)
*C04B 41/87* (2006.01)

(52) U.S. Cl.
CPC .......... *C04B 35/6261* (2013.01); *C04B 35/64* (2013.01); *C04B 41/87* (2013.01); *C04B 2235/3244* (2013.01); *C04B 2235/661* (2013.01); *C04B 2235/945* (2013.01); *C04B 2237/341* (2013.01); *C04B 2237/343* (2013.01); *C04B 2237/52* (2013.01)

(58) Field of Classification Search
USPC ................ 427/2.1; 264/16; 433/199.1, 201.1
See application file for complete search history.

APPARATUS AND METHOD FOR IMPROVING ADHESIVE STRENGTH OF DENTAL RESTORATION

CROSS-REFERENCE TO RELATED APPLICATION(S)

This application is based upon and claims the benefit of priority of prior Korean Patent Application No. 10-2015-0159264, titled "Dental Restoration Material having Improved Adhesive Strength and Manufacturing Method of the Same," filed on Nov. 13, 2015, the entire content of which is incorporated herein by reference.

TECHNICAL FIELD

The present disclosure relates to restorative dentistry and, in particular, to methods and systems for manufacturing devices including dental restorations with improved durability and enhanced adhesive strength between a porcelain layer and a zirconia based crown and between an abutment tooth and the zirconia based crown.

BACKGROUND

The word "dental restoration" as used herein may refer to one or more procedures, and/or resulting products there of, for restoring a structure of one or more teeth damaged by decay. The dental restoration may be performed using various dental restorative materials which may have various shapes and/or features.

The dental restoration may include dental fillings, structures, or casts that may be used in replacing damaged tooth structures. Traditional dental restorations may be manufactured using materials comprising a metal or a resin (sometimes may be referred to as "metal and/or resin restoration") and generally may lack adequate strength and aesthetic aspects. Further, the traditional dental restorations may lead to discoloration or fracture there of and such metal and/or resin restorations may be cosmetically not appealing or attractive for use on teeth such as maxillary anterior teeth.

In producing or manufacturing traditional type dental restorations, precious metal alloys such as gold alloys have been widely used in dental veneers, inlays, on lays, stumps, crowns, and the like. However, the cost of manufacturing the dental restorations using precious metals may be very high and may increase dramatically based on varying prices of the precious metals (e.g., gold) in the market. Moreover, the precious metal alloys may have different colors from those of natural teeth and, as a result, may be undesirable to many people as dental restorations for such cosmetic reasons.

With rising standards of living, people's expectations have been increasing for an aesthetic aspect of their dental restorations. By way of example, for dental restorations that may encase an entire visible portion of a tooth such as a crown, ceramic type restorations have been preferred and gained popularity over existing metal alloy-based restorations.

The preference for ceramic-based restorations, which can provide desirable properties such as greater strength and durability, has also led to increased use of zirconia ($ZrO_2$) in dental restorations ("zirconia-based restorations"). An aesthetic appeal of the zirconia-based restorations may be limited, however, because of their turbid surface color. Despite such disadvantages, use of zirconia-based restorations has continued to rise. Use of zirconia-based restorations are documented in literature, including patent publications, Korean Patent Publication No. 10-2005-0084293, titled "Abutment for a dental implant, dental implant comprising such an abutment, and method for the production of dentures by means of said dental implant," Korean Patent Publication No. 10-2008-0094625, titled "Process for providing a topography to the surface of a dental implant," the entire contents of which are incorporated herein by reference. Also, use of etching solutions of the zirconia-based restorations is documented in Korean Patent Publication No. 10-2013-0138578, titled "Method for surface treatment of tooth restoration, and tooth restoration there from," issued to one of the inventors of the present application, the entire content of which is incorporated herein by reference.

However, there is still a further need for improved and more efficient technology for producing and manufacturing the zirconia-based dental restorations with enhanced adhesive strength and durability, and for methods and systems for more safe manufacture of the zirconia-based dental restorations, than existing technology.

SUMMARY

In various aspects of the present disclosure, durability and adhesive strength of implant devices such as zirconia-based implant devices or product(s) and manufacturing processes there of are further enhanced and improved. By way of example, the present disclosure provides various aspects of an improved etching compound including a solution and/or a gel. Further, the present disclosure provides various aspects of improved manufacturing processes, techniques, and/or systems for treating surfaces of the zirconia-based implant devices using the etching solution and various devices. In the description below, a zirconia-based implant device may include a zirconia based crown (or a zirconia crown) for dental restoration purposes, for an illustrative purpose, but the present technology is not limited there to, and may include other implant devices and purposes. Further, although the present technology discloses embodiments of a 100% zirconia based crown, it may not be limited there to and may include other substances in addition to zirconia.

In an aspect of the present disclosure, an embodiment of a zirconia based crown may include a first surface and a second surface. The first surface of the zirconia based crown is configured to adjoin a top surface of an abutment tooth and the second surface of the zirconia based crown is configured to adjoin a porcelain layer that is built upon on a top portion of the zirconia based crown. The zirconia based crown may be etched, embossed, or impressed by a surface treatment technique, for example, to enhance the adhesion between the abutment tooth and the zirconia based crown and between the zirconia based crown and the porcelain layer disposed on the top portion of the zirconia based crown.

Surface treating or embossing may increase surface friction and roughness which, in turn, may increase adhesion between the abutment tooth and the zirconia based crown as well as between the zirconia based crown and the porcelain layer. As a result, the dental restoration may be secured to the top of the abutment tooth, thereby reducing movements or peeling of the dental restoration. Enhanced adhesion thus may prevent peeling and increase wear resistance, further improving the durability of the dental restoration.

In another aspect of the present disclosure, the porcelain layer may be maintained at a minimum thickness while a thickness of the zirconia based crown, which has excellent mechanical properties, may be varied to a desirable thickness, providing a dental restoration having both aesthetic and mechanical advantages.

In one aspect of the present disclosure, a method of producing a dental restoration is provided, in which the dental restoration includes a zirconia based crown that is to be bonded to the top of an abutment tooth and a porcelain layer that is built-up on the top of the zirconia based crown. By way of example, at a high level, a zirconia based crown is produced or manufactured in a following manner. First, a zirconia or zirconia-based block is processed, milled, and/or molded to form a molded zirconia based crown having dimensions that are smaller than outer dimensions of an abutment tooth on which the molded zirconia based crown is to be applied. The molded zirconia based crown having a first surface and a second surface may then be sintered. The first surface is configured to be bonded to the top of the abutment tooth and the second surface is configured to receive and be bonded to one or more layered porcelain build-ups. The first and second surfaces of the zirconia based crown are surface treated or etched using a surface treatment or etching solution in accordance with an aspect of the present disclosure.

In an aspect of the present disclosure, the surface treatment solution includes at least nitric acid ($HNO_3$), hydrofluoric acid (HF), and hydrogen peroxide ($H_2O_2$). For the etching of the surfaces, for safe procedures, examples embodiments of etching devices are disclosed herein. In an aspect of the present disclosure, the zirconia based crown may be placed in a second contained and then placed in a first container including an etching or surface treatment solution such that the zirconia based crown is immersed in the surface treatment or etching solution. The first surface and the second surface of the zirconia based crown are completely exposed to the surface treatment solution. After the etching procedure, the surface treated zirconia based crown is then removed from the surface treatment solution by removing the second container from the first container and then cleaned. After the cleaning of the zirconia based crown, porcelain layers may be built on the top of the cleaned zirconia based crown and the resultant zirconia based crown having the porcelain build-up is then sintered as a final dental restoration. In the example, the porcelain layer may include feldspathic porcelain containing 40-85% by weight of feldspar and 5-30% by weight of clay.

As such, a dental restoration based on the resultant zirconia based crown may be obtained with much improved and enhanced bonding strength for the first and second surfaces of the zirconia based crown.

In an aspect of the present disclosure, the surface treatment solution described herein may include acetyl chloride ($CH_3COCl$), in addition to nitric acid ($HNO_3$), hydrofluoric acid (HF), and hydrogen peroxide ($H_2O_2$). Further, it may be desirable for the surface treatment solution to include acetyl chloride between about 0.001% and about 10% by weight.

In another aspect of the present disclosure, the surface treatment solution may include oxalyl chloride ($C_2O_2Cl_2$), in addition to nitric acid ($HNO_3$), hydrofluoric acid (HF), and hydrogen peroxide ($H_2O_2$). Further, it may be desirable for the surface treatment solution to include oxalyl chloride between about 0.001% and about 10% by weight.

It may be also desirable for the surface treatment solution to include at least nitric acid ($HNO_3$) and hydrofluoric acid (HF) in such a manner that a ratio of a volume of nitric acid to a volume of hydrofluoric acid in the surface treatment solution ranges between about 1:0.1 and about 1:4. Further, it may be desirable for the surface treatment solution to include hydrogen peroxide between about 0.1% and about 20% by weight.

Further, in an aspect, the present technology or methodology described herein may include an ultrasonic impact treatment in addition to the etching procedure. The ultrasonic impact treatment may use an ultrasonic signal having a frequency between about 20 kHz and about 60 kHz at an intensity level between about 1 $W/cm^2$ and about 50 $W/cm^2$. In the example, it is noted that the ultrasonic impact treatment using the ultrasonic signal having a frequency between about 30 kHz and about 50 KHz at an intensity level between about 0.2 $W/cm^2$ and about 1 $W/cm^2$ may be used for best or optimal results (e.g., surface roughness and a short etching during).

In another aspect of the present disclosure, the surface treatment may be performed on the zirconia based crown for a duration between about 10 minutes and about 90 minutes. Furthermore, when the ultrasonic impact treatment is used while the zirconia based crown is etched in the surface treatment solution, a total duration for desired results may be shortened compared to using the etching operation alone (e.g., about two hours).

Further, the surface treated zirconia based crown may be cleaned as follows. The second container including the surface treated zirconia based crown is removed from within the first container and may be placed in a cleaning fluid. The cleaned, surface treated zirconia based crown may be removed from inside the second container.

Furthermore, the surface treatment process, in accordance with an aspect of the present disclosure, may require relatively a small amount of time compared to the existing technologies, resulting in an increased process efficiency and increased safety. Further, the surface treatment process in accordance with the present disclosure may be carried out at a room temperature and still yield favorable results, providing further advantages over the existing technologies for the surface treatment.

In another aspect of the present disclosure, use of a first container containing the surface treatment or etching solution and a second container including a plurality of holes and having a smaller diameter than the first container such that the second container may be seated entirely inside the first container may further increase process safety and allow easy performance of the surface treatment process using the surface treatment or etching solution which may be highly hazardous to people who perform the etching procedures to obtain dental restorations with desired characteristics.

These and other aspects of the present disclosure will become more fully understood upon a review of the detailed description, which follows.

BRIEF DESCRIPTION OF THE DRAWINGS

A more detailed understanding may be obtained from the following description in conjunction with the accompanying drawings.

DETAILED DESCRIPTION

Figure 1:
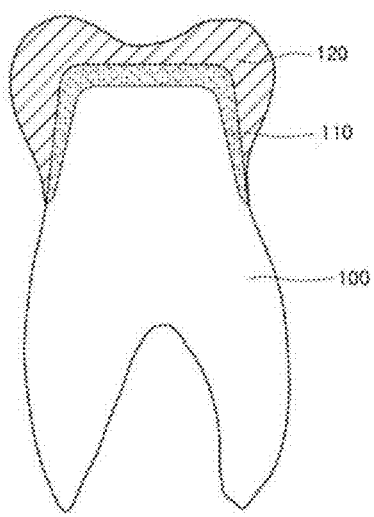
FIG. 1 illustrates a cross-sectional view of an example of a dental restoration in accordance with an aspect of the present disclosure.

The detailed description of illustrative examples will now be set forth below in connection with the various drawings. The description below is intended to be exemplary and in no way limit the scope of the claimed invention. It provides a detailed example of possible implementation, and is not intended to represent the only configuration in which the concepts described herein may be practiced. As such, the detailed description includes specific details for the purpose of providing a thorough understanding of various concepts, and it is noted that these concepts may be practiced without these specific details. In some instances, well known structures and components are shown in block diagram form in order to avoid obscuring such concepts. It is noted that like reference numerals are used in the drawings to denote like elements and features.

By way of example, the present disclosure provides descriptions of how to prepare and manufacture a dental restoration with enhanced adhesiveness and durability of a zirconia based crown. In the present disclosure, the word "zirconia based crown" may be interchangeably used herein to refer to a "zirconia crown" unless otherwise noted differently. The present disclosure further provides descriptions of apparatuses and devices for treating surfaces of the zirconia based crown and a surface treatment solution for use on the zirconia based crown. It is noted that although the examples provided herein are, for the illustrative purposes only, examples of the zirconia based crown and the apparatuses and devices for treating the surfaces of the zirconia based crown and the surface treatment solution for obtaining dental restorations, the present technology disclosed herein is not limited there to, and may be applicable to other types of zirconia based implant devices.

In an aspect of the present technology, in order to take advantages of desirable mechanical properties such as strength and durability, zirconia ($ZrO_2$) is used as a ceramic ingredient in manufacturing implant devices including dental implants for dental restoration purposes. A zirconia block, however, has a turbid surface color, which may limit its aesthetic appeal for a dental restoration. As such, in an aspect of the present disclosure, rather than using zirconia as an exclusive ingredient or substance in manufacturing a dental restoration, the present technology provides the dental restoration including porcelain layers built-up on a top of the zirconia (or zirconia based) crown.

In the example, various layering methods may be used to build up porcelain layers on the top of the zirconia crown using porcelain powder. By way of example, the porcelain powder may be mixed with a solvent (e.g., water) to give a slurry or paste, and a brush may be used to coat the surfaces of the zirconia crown with the slurry or paste.

Further, using common dental restoration processing techniques, a zirconia crown may be produced. By way of example, a shape of a tooth may be determined by generating a three-dimensional model, and a Computer Aided Design/Computer Aided Manufacturing (CAD/CAM) dental restoration may be milled from a solid zirconia block to closely match a shape of a tooth. In the example, any commercially available blocks of solid zirconia may be used.

The zirconia crown with porcelain layers built-up or positioned on the top of the zirconia crown is then sintered to produce an end product, for example, a final dental restoration for a patient.

FIG. 1 illustrates an example of a cross-section of such a dental restoration. The dental restoration may include an abutment tooth 100, a zirconia crown 110, and one or more porcelain layers 120. The zirconia crown 110 may be bonded to the top of the abutment tooth 100. The one or more porcelain layers 120 is built up on the top of the zirconia crown 110.

In the example of FIG. 1, the zirconia crown 110 may have a thickness of approximately 0.8 mm (millimeters) and the one or more porcelain layers 120 may have a thickness of 0.6-1.2 mm. It is noted that as the thickness of the one or more porcelain layers, which has a relatively small internal pressure (i.e., approximately 400 MPa), is not smaller than the thickness of the zirconia crown (i.e., internal pressure of 900-1200 MPa), a dental restoration may not provide desirable levels of strength and durability. On the other hand, a significant reduction in the thickness of the one or more porcelain layers 120 may result in inadequate bonding strength (or interfacial adhesion) between the zirconia crown 110 and the one or more porcelain layers 120. Further, if the adhesion between the abutment tooth 100 and the zirconia crown 110 is inadequate, shock or stress applied to the tooth may cause the zirconia crown to peel off and/or the wear resistance to be lessened, thereby reducing the durability of the dental restoration.

Figure 2:
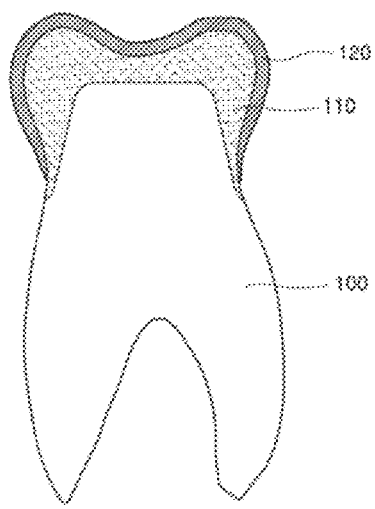
FIG. 2 illustrates a cross-sectional view of an example of the dental restoration of FIG. 1.

FIG. 2 illustrates another example of a cross-section of an example of a dental restoration in accordance with an aspect of the present disclosure. In the example, the zirconia crown 110 is bonded to the top of the abutment tooth 100, and one or more porcelain layers 120 are built up on the top of the zirconia crown 110. In an aspect of the present disclosure, if there is adequate adhesion between the one or more porcelain layers 120 and the zirconia crown 110, the one or more porcelain layers 120 can be kept relatively thin. For example, in one implementation, the zirconia crown 110 may have a thickness of 0.5-1.2 mm while the one or more porcelain layers 120 may be kept at a thickness of 0.1-0.5 mm. In the examples, if the adhesion between the abutment tooth 100 and the zirconia crown 110 is inadequate, shock or stress applied to the tooth may cause the zirconia crown to peel off and/or the wear resistance to be lessened, thereby reducing the durability of the dental restoration. As such, the increased adhesive strength or bonding strength may increase the durability of the dental restoration.

In the descriptions below, various aspects of the present disclosure including a method and system for manufacturing or producing a dental restoration with enhanced adhesive strength and durability are provided herein. As noted above, as an initial matter, solid zirconia blocks are processed to mold a zirconia crown 110 that has dimensions that are smaller than outer dimensions of the abutment tooth 100.

The molded zirconia crown is then baked to result in the zirconia crown 110 having a first surface and a second surface. In the example, the first surface of the zirconia crown 110 is to adjoin a top surface of the abutment tooth 100 and the second surface of the zirconia crown 110 is to receive the one or more porcelain layers built-up on the second surface of the zirconia crown 110. Further, in the example, the one or more porcelain layers may include feldspathic porcelain containing 40-85% by weight of feldspar and 5-30% by weight of clay.

In an aspect of the present disclosure, a surface treatment or etching solution is prepared, which contains at least nitric acid ($HNO_3$), hydrofluoric acid (HF) and hydrogen peroxide ($H_2O_2$). Using the surface treatment solution and various etching systems disclosed herein, the first and second surfaces of the zirconia crown are etched. That is, the first and second surfaces of the zirconia crown are exposed to the surface treatment solution such that the first and second surfaces of the zirconia crown are embossed.

In an aspect of the present disclosure, the zirconia crown may be immersed in the surface treatment solution using a second container (as shown in FIGS. 4-6) and a first container including the surface treatment solution. Further, while the zirconia crown is etched in the surface treatment or etching solution, via the first and second containers, an ultrasonic impact treatment may be applied to the zirconia crown for a certain period of time, e.g., an hour. It is noted that based on various trials and experiments, the ultrasonic impact treatment may facilitate the etching process and shorten a total duration for the surface treatment process. Also, alternatively, the ultrasonic impact treatment may be applied after the surface treatment of the zirconia crown, e.g., after the zirconia crown is taken out of the surface treatment solution.

In one implementation, the ultrasonic impact treatment may use an ultrasonic signal having a frequency between about 1 kHz and about 40 kHz at an intensity level between 1 $W/cm^2$ and 50 $W/cm^2$. Further, in an aspect of the present disclosure, for the best results, the ultrasonic impact treatment using an ultrasonic signal having a frequency selected between about 30 kHz and about 50 KHz at an intensity level between about 0.2 $W/cm^2$ and about 1 $W/cm^2$ may be used for the best results.

After the surface treatment of the zirconia crown 110, the surface treated zirconia crown 110 may be removed for cleaning from the surface treatment solution by taking out the second container from inside the first container which contains the surface treatment or etching solution. The cleaning may be done on the surface treated zirconia crown 110 using a cleaning solution, such as water, steam, or the like to remove any residuals from the surfaces of the zirconia crown 110.

One or more porcelain layers 120 are then built up on the top of the cleaned zirconia crown 110, resulting in a composite zirconia crown structure, that is, a structure including the zirconia crown 110 and the one or more porcelain layers 120, and the resulting composite zirconia crown structure is then sintered for obtaining a final dental restoration product. As a result of the surface treatment techniques and devices and apparatuses for per forming the surface treatment described herein, the adhesion strength of the first and second surfaces of the zirconia crown 110 may be enhanced and the etching procedures or operations may be made more safe and convenient.

As noted earlier, in an aspect of the present disclosure, the surface treatment or etching solution may include at least nitric acid ($HNO_3$), hydrofluoric acid (HF) and hydrogen peroxide ($H_2O_2$). Further, the surface treatment solution may include acetyl chloride ($CH_3COCl$) by a certain amount, e.g., acetyl chloride of between about 0.001% and about 10% by weight. Acetyl chloride is an acid chloride derived from acetic acid and belongs to a class of organic compounds called acyl halides, which is a colorless, corrosive, and volatile liquid. The addition of Acetyl chloride may further increase the performance characteristics of the surface treatment or etching solution (e.g., surface roughness or an etching time).

In another aspect of the present disclosure, the surface treatment solution may further include oxalyl chloride ($C_2O_2Cl_2$). It may be desirable for the surface treatment solution to contain a certain amount of oxalyl chloride between about 0.001% and about 10% by weight. Oxalyl chloride is a chemical compound which is colorless, sharp-smelling liquid. The addition of Oxalyl chloride may further increase the performance characteristics of the surface treatment or etching solution (e.g., surface roughness or an etching time).

In an aspect of the present disclosure, it is desirable for the surface treatment solution to include nitric acid ($HNO_3$) and hydrofluoric acid (HF) such that a ratio of a volume of nitric acid to a volume of hydrofluoric acid in the surface treatment solution may range between about 1:0.1 and about 1:4. Further, it may be desirable for the surface treatment solution to include a certain amount of hydrogen peroxide between about 0.1% and about 20% by weight.

Furthermore, regarding a time duration for the surface treatment or etching operation, it may be desirable to perform the surface treatment for the time duration of between about 10 minutes and about 90 minutes. As noted above, the ultrasonic impact treatment in conjunction with the etching operation may shorten the time duration for the surface treatment of the zirconia based crown, e.g., reduce the time duration from a couple of hours to less than an hour.

Figure 3:
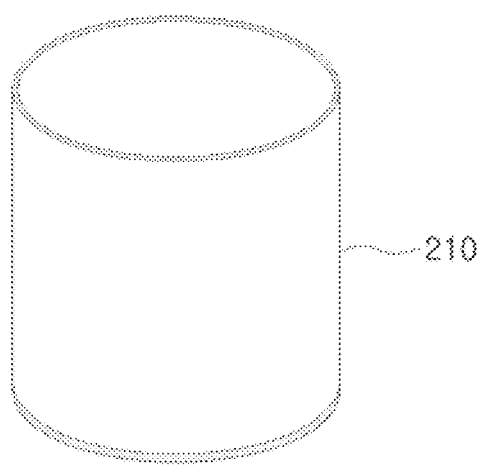
FIG. 3 illustrates an example of a first container in accordance with an aspect of the present disclosure.

As an example, in another aspect of the present disclosure, a brief description of a surface treatment process is provided below, at a high level. A surface treatment or etching solution is prepared in accordance with an aspect of the present disclosure. The surface treatment or etching solution is placed in a first container. An example of the first container is shown in FIG. 3. A zirconia crown (that is to be etched) is set or placed in a second container that has a smaller diameter than the first container and has a plurality of holes defined on at least one of a bottom surface and a sidewall of the second container. The examples of the second container are shown in FIGS. 4-6. The second container is then inserted in the first container such that at least a portion of the zirconia crown in the second mesh container may be soaked in the surface treatment solution that enters the second container through the plurality of holes defined on the at least one of the bottom surface and the sidewall of the second container.

After the surface treatment or etching procedures, the surface treated zirconia crown (e.g., the embossed zirconia crown) may then be cleaned as follows. The second container containing the etched zirconia crown is removed from the first container and is then placed in a cleaning fluid such that the zirconia crown inside the second container may be cleaned in the cleaning fluid. After the cleaning, the zirconia crown may be removed from the second container. For the cleaning operation, various techniques including techniques using water, steam, or the like may be applied to the zirconia crown.

As a result, the present technology described herein provides a dental restoration comprising a zirconia crown to be bonded to a top of an abutment tooth and layered porcelain build-ups on the top of the zirconia crown. In the example, the zirconia crown may have dimensions that are smaller than the outer dimensions of the abutment tooth. Also, a first surface of the etched zirconia crown is to adjoin the top surface of the abutment tooth and a second surface of the etched zirconia crown which is configured to receive the layered porcelain build-ups.

By way of example, preferred embodiments methods and apparatuses for manufacturing dental restorations with increased adhesive strength or bonding strength in accordance with the present technology are described below in greater detail.

A shape of a tooth (a target tooth) may be determined using any of the existing methods including a three-dimensional modeling method (e.g., 3-D optical impression using a 3-D optical camera, etc.). A shape of the zirconia crown, e.g., 110 is to be determined with a view to a thickness of the one or more porcelain layers 120 to be built up on the top of the zirconia crown. It may be desirable to keep the dimensions of the zirconia crown smaller than outer dimensions of the target tooth. By way of example, the dimensions of the zirconia crown 110 may be 0.1-0.5 mm smaller than the outer dimensions of the target tooth 100.

Further, the zirconia crown 110 may be computer aided design/compute aided manufacturing (CAD/CAM) milled from one or more solid zirconia blocks to closely resemble a determined shape of the target tooth 100.

In one example, the one or more zirconia blocks may be made as follows. Zirconia powder may be used to press mold and sintered to produce the zirconia blocks. Alternatively, commercially available zirconia blocks such as "3Y-PSZ" (which is used in making artificial teeth) may be used. "3Y-PSZ" or partially-stabilized-zirconia has numerous desirable characteristics, such as strength, heat stabilization, and high corrosion resistance. Further, various other commercialized zirconia blocks may also be used for the purposes of the present disclosure. Several companies, including D-MAX, HASS, SB and ACUCERA, each provide their own commercial versions of zirconia blocks which may be used for the present disclosure. Further, ZirBlank by ACUCERA may be used as a zirconia block for the present technology.

In an aspect of the present disclosure, a molded composite structure may be sintered to form the zirconia crown 110. The sintered zirconia crown 110 may have dimensions that are smaller than the required outer dimensions of the target tooth 100. In the example, the sintering process may be preferably carried out at a temperature of about 1450° C.-1650° C. for a time duration of between about 1 hour and about 24 hours.

Having the zirconia crown 110 prepared in a manner described above, the zirconia crown 110 is subjected to a surface treatment process (or an etching process) using a surface treatment solution. In an aspect of the present disclosure, the surface treatment solution includes at least nitric acid ($HNO_3$), hydrofluoric acid (HF) and hydrogen peroxide ($H_2O_2$) in a predetermined proportion. In an aspect of the present disclosure, the surface treatment solution may include acetyl chloride ($CH_3COCl$). The acetyl chloride may facilitate the surface treatment process. Also, it may be desirable for the surface treatment solution to include acetyl chloride between about 0.001% and about 10% by weight.

In another aspect of the present disclosure, alternatively or in addition to, the surface treatment solution may include oxalyl chloride ($C_2O_2Cl_2$). The oxalyl chloride may also facilitate the surface treatment process and improve the surface characteristics of the zirconia crown. It may be desirable for the surface treatment solution to include oxalyl chloride between about 0.001% and about 10% by weight.

One or more surfaces of the zirconia crown 110 which may come in contact with the porcelain layer 120 and the abutment tooth 100, respectively, may be treated by the etching solution or embossing. For the surface treatment of the zirconia crown 110, various technologies may be used. In an aspect of the present disclosure, the zirconia crown 110 may be treated with the surface treatment solution described herein. By way of example, the zirconia crown 110 may be immersed in the surface treatment solution so as to expose both of the surfaces (e.g., the first surface and the second surface) of the zirconia crown to the surface treatment solution for the etching or surface treatment. In the present disclosure, the first surface of the zirconia crown 110 is configured to adhere to the abutment tooth 100 and the second surface of the zirconia crown 110 is configured to receive the one or more porcelain layers built-up on the zirconia crown 110.

In an aspect of the present disclosure, when treating the first and second surfaces of the zirconia crown 110, an ultrasonic impact treatment using an ultrasonic signal may be used in conjunction with the etching or surface treatment process. The word "ultrasonic signals" used herein refers to sound waves or signals with frequencies between about 1 kHz to about 60 kHz, preferably between about 10 kHz and about 30 kHz. The ultrasonic impact treatment using such a frequency may allow the surfaces of the zirconia crown 110 to be treated uniformly and help to reduce an amount of time required for the surface treatment of the zirconia crown. Further, an ultrasonic signal having a frequency between about 10 kHz and 30 kHz at an intensity level between about 1 $W/cm^2$ and about 50 $W/cm^2$ may be used. Furthermore, in an aspect of the present disclosure, the ultrasonic signal having a frequency selected between about 30 kHz and about 50 KHz at an intensity level between about 0.2 $W/cm^2$ and about 1.0 $W/cm^2$ may be used for optimal results.

Through numerous trials and errors, it is determined that using the nitric acid ($HNO_3$) or hydrofluoric acid (HF) alone or in combination may cause etching speeds to be slow and found by the inventors that using an etching solution including at least nitric acid ($HNO_3$), hydrofluoric acid (HF) and hydrogen peroxide ($H_2O_2$) may result in superior surface treatment effects and significantly shorten the time for the surface treatment of a zirconia crown. That is, the surface treatment or etching solution having at least nitric acid, hydrofluoric acid, and hydrogen peroxide is found to be superior in performance and results to a mixture or solution including only nitric acid and hydrofluoric acid.

Further, as noted above, an ultrasonic impact treatment may be used to facilitate the entire process, when used in conjunction with the surface treatment solution including at least nitric acid, hydrofluoric acid and hydrogen peroxide to yield the best results. For example, using the ultrasonic impact treatment in conjunction with the use of the surface treatment solution may reduce the time for treating the surfaces of the zirconia crown by at least one hour, thereby reducing the surface treatment time as well as reducing the time for exposing users to the surface treatment solution.

Further, in an aspect of the present disclosure, it is desirable for the surface treatment solution to include at least nitric acid and hydrofluoric acid, with a ratio of a volume of nitric acid to a volume of hydrofluoric acid in a solution range between 1:0.1 and 1:4 (and more preferably, between 1:0.5 and 1:1.5). Further, it may be also desirable for the surface treatment solution to include between about 0.1% and about 20% (more preferably, between about 5% and about 15%) by weight of hydrogen peroxide.

It is also noted that if the content of hydrofluoric acid is too low relative to that of nitric acid, the surface treatment process may proceed very slowly (or take a long time). On the other hand, if the hydrofluoric acid content is too high relative to the nitric acid content, a hardness of a surface of the zirconia crown may be reduced. Further, if the hydrogen peroxide content is too low, it may take a long time to treat and obtain desirable characteristics of the surfaces of the zirconia crown. If the hydrogen peroxide content is too high, the surfaces of the zirconia crown may be non-uniformly/unevenly treated.

Further, it is noted that the above ratio of a volume of nitric acid to a volume of hydrofluoric acid used herein refers to a volume of acids that are present in an aqueous solution (which is also interchangeably referred to herein as the "surface treatment solution").

In an aspect of the present disclosure, it may be desirable to immerse the zirconia crown 110 in the surface treatment solution at a room temperature for about 10 to 90 minutes. Further, it is noted that if a time for treating the surfaces of the zirconia crown (or a "surface treating time") is less than about 10 minutes, the adhesive strength of the surfaces of the zirconia crown 110 may be undesirably low, while the surfacing treating time that is greater than about 90 minutes may cause excessive etching and make the zirconia crown 110 to be too thin and as a result reduce the hardness of the zirconia crown 110.

Further, it has been found that, in accordance with an aspect of the present disclosure, at the room temperature, the surface treatment using the surface treating solution including at least nitric acid, hydrofluoric acid and hydrogen peroxide may yield good results. It is also noted that existing technology for chemically etching zirconia based crowns or blocks typically involve using an etching solution including calcium sulfate or phosphate at very high temperatures, e.g., temperatures greater than 400° C. Etching at such high temperature may pose serious safety risks to users. However, in accordance with some aspects of the present disclosure, the surface treatment or etching solution disclosed herein may allow the surface treatment process to be performed at a room temperature while yielding very favorable results at a safer operating environment.

As noted above, the surface treatment solution of the present disclosure may additionally include acetyl chloride and oxalyl chloride. These chemical ingredients of the surface treatment solution may be dangerous to those performing the surface treatment processes on zirconia crowns. As such, additional devices or apparatuses may be used during the surface treatment process of zirconia crowns.

FIGS. 3-7 show example devices of the additional devices or apparatuses, which may be used to facilitate and improve safety of the users during the surface treatment process of the zirconia based crowns.

Figure 4A:
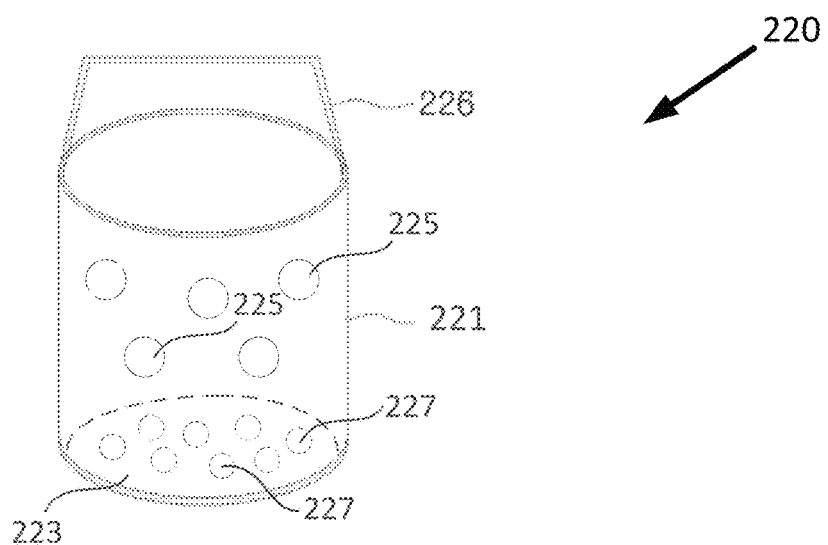
FIGS. 4A and 4B illustrate an example of a second container in accordance with an aspect of the present disclosure.
Figure 4B:
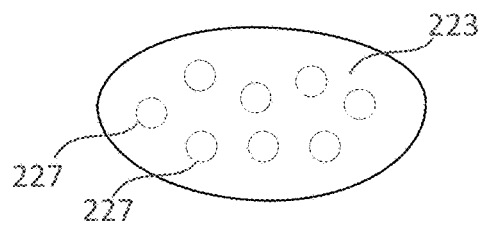
Figure 5A:
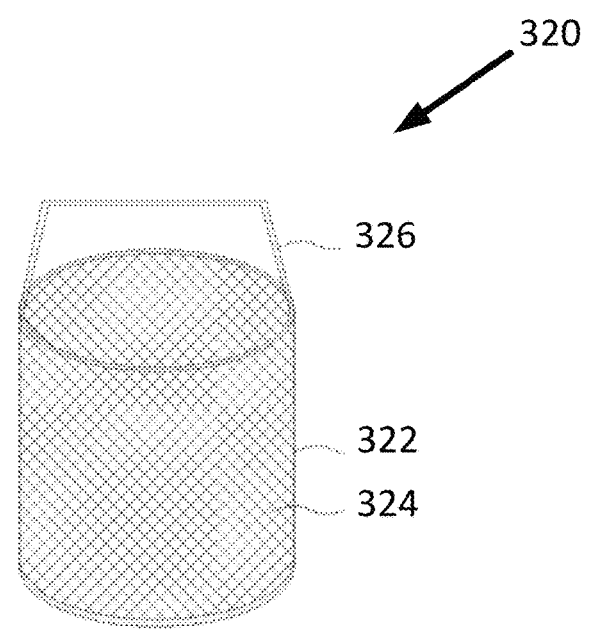
FIGS. 5A and 5B illustrate an example of a second container in accordance with an aspect of the present disclosure.
Figure 5B:
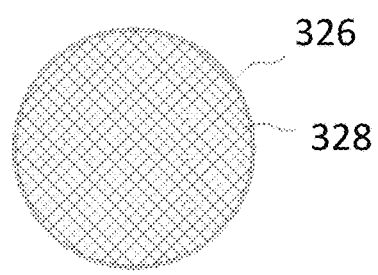
Figure 6A:
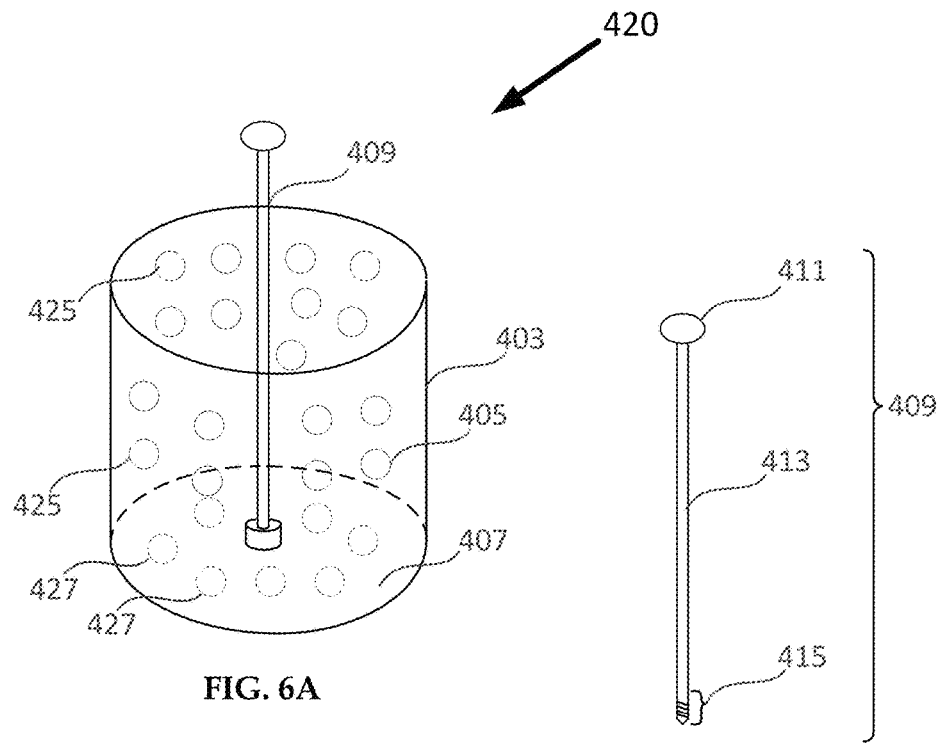
FIGS. 6A and 6B illustrate an example of another embodiment of a second container in accordance with an aspect of the present disclosure.
Figure 6B:
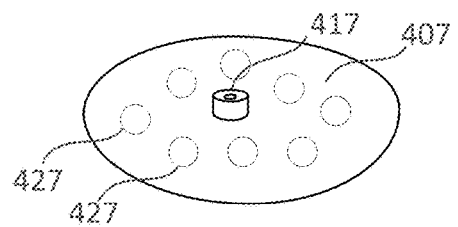
Figure 7:
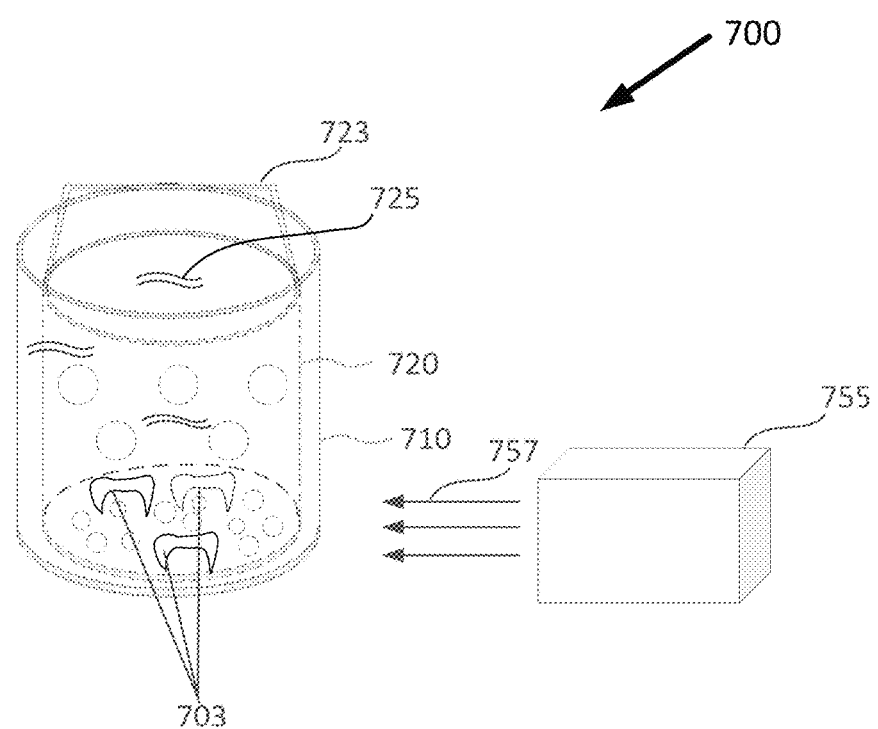
FIG. 7 illustrates a perspective view showing examples of a system in accordance with an aspect of the present disclosure.

FIG. 3 illustrates a perspective view of an example of a first container 210 or 710 (which is interchangeably referred to herein as an outer container). FIGS. 4A and 4B illustrate example diagrams of a second container (which may be interchangeably referred to herein as an inner container or a second mesh container or the like, i.e., 220, 320, 420, 720) in an aspect of the present disclosure. FIGS. 5A and 5B illustrate another example of a second container in an aspect of the present disclosure. FIGS. 6A and 6B illustrate another example of the second container in an aspect of the present disclosure. FIG. 7 illustrates an example system or apparatus for per forming etching procedures on zirconia based crowns in aspects of the present disclosure.

As shown in FIGS. 3-7, an example of a device or system may be used in a surface treatment process for zirconia crowns (which is interchangeably referred to herein as the "zirconia surface treatment device"). In an aspect of the present disclosure, the zirconia surface treatment device may include a first container 210 (or 710) which is configured to hold a surface treatment solution and a second container 220 (or 320, 420, 720) which may be disposed inside the first container 210 (or 710). That is, the second container 220 (or 320, 420, 720) with a zirconia crown (that is to be etched) may be inserted or placed in the first container 210 (or 710) for desired etching procedures. Both the first container 210 (or 710) and the second container 220 (or 320, 420, 720) may be made of a material that is resistant to acids and acidic chemical compounds. By way of example, the first container 210 (or 710) and the second container 220 (or 320, 420, 720) may be made of a high-density polyethylene (HDPE) material which are industrial grade acid resistant materials. Alternatively, other acid resistant materials may be used to construct the first container 210 (or 710) and the second container 220 (or 320, 420, 720).

FIGS. 4A and 4B illustrate an example of an embodiment of a second container in accordance with an aspect of the present disclosure. As shown in FIG. 4A, a second container 220 includes a side portion 221, a bottom portion 223, and a handle 226. The side portion 221 of the second container 220 may have a plurality of holes 225 defined on a surface of the side portion 221, and a plurality of holes 227 on a surface of the bottom portion 223 as shown in FIG. 4B. In the example, the plurality of holes 225 and 227 are defined on the side and bottom portions of the second container 220 such that a surface treatment solution may flow into inside the second container 220 from the first container 210, when the second container 220 is placed inside the first container 210 to etch surfaces of a zirconia based crown placed on the bottom portion 223 of the second container 220. That is, the zirconia based crown will be completely immersed in the etching solution or the surface treatment solution for a desired etching operation.

FIGS. 5A and 5B illustrate another example of an embodiment of the second container in accordance with an aspect of the present disclosure. In the example, a second container 320 may include a plurality of mesh type holes 324 forming a mesh on a side wall portion 322 as shown in FIG. 5A and the plurality of holes 328 forming a mesh on a bottom portion 326 of the second container 220, as shown in FIG. 5B.

FIGS. 6A and 6B illustrate another example of an embodiment of the second container in accordance with an aspect of the present disclosure. In the example, a second container 420 may include a side wall portion 403, a bottom portion 407, and a rod portion 409 coupled to the bottom portion 407. The side wall portion 403 includes a plurality of holes 405 and the bottom portion 407 includes a plurality of holes 427, as shown in FIGS. 6A and 6B. Further, the rod portion 409 includes a handle 411, a body 413, and a coupling portion 415. The coupling portion 415 includes one or more threads so as to be securely coupled to the bottom portion 407 via a receptacle portion 417 as shown in FIG. 6B. It is noted that the one or more threads are just one example of the embodiment in an aspect of the present disclosure. Alternatively, other interlocking mechanisms without using the one or more threads may be used to securely couple the rod portion 407 to the bottom portion 407 of the second container 420.

Users may hold the handle 411 to place the second container 420 with one or more zirconia based crowns (not shown) into the first container 210 containing an etching solution or surface treatment solution to etch or treat surfaces of the one or more zirconia based crowns. After the etching or surface treatment of the one or more zirconia based crowns, the users may hold the handle 411 of the second container 420 and remove the second container 420 from the etching solution inside the first container 210 for one or more cleaning steps.

FIG. 7 illustrates an example of a system or apparatus for per forming an etching or surface treatment process in an aspect of the present disclosure. As shown in FIG. 7, a first container 710 contains an etching or surface treatment solution 725 in accordance with an aspect of the present disclosure, and a second container 720 with zirconia based crowns 703 is placed inside the first container 710 such that the zirconia based crowns 703 are completely immersed inside the etching or surface treatment solution 725. As shown in FIG. 7, an outer diameter of the second container 720 may be smaller than an inner diameter of the first container 710 such that the second container 720 can be positioned or disposed completely within an inner space of the first container 710. Further, the second container 720 includes a handle portion 723 which may be coupled (or attached) to an upper portion of the second container 720 to facilitate removal of the second container 720 from the first container 710.

Alternatively, in other implementations, the first container such as one 710 and the second container such as one 720 may take other shapes and forms, e.g., rectangular or other geometric shapes, so long as the first container and the second container are configured such a way that the second container is to be disposed inside the first container which contains the etching or surface treatment solution. Alternatively, the zirconia based crowns may be etched without using the second container by just dipping the zirconia based crowns in the etching or surface treatment solution in the first container.

For the etching or surface treatment process, the zirconia based crowns such as the ones 703 may be etched for a predetermined period of time, for example, 30 minutes to a couple of hours for desired adhesive strength and/or surface results, as shown in Table 1 below. Alternatively, an ultrasonic impact treatment may be used in conjunction with the etching process to facilitate the etching process. In the example, as shown in FIG. 7, an example of an ultrasonic impact device 755 may be used while the zirconia based crows are etched in the etching or surface treatment solution 725 inside the first container 710 and the second container 720. Through numerous experiments, it is found that an ultrasonic impact treatment may be used to facilitate and shorten a time for treating the surfaces of the zirconia based crown in the etching or surface treatment solution in accordance with an aspect of the present disclosure. By way of example, the ultrasonic impact device 755 is configured to generate an ultrasonic signal 757 having a predetermined frequency, e.g., a frequency selected from a range from about 1 kHz to about 40 kHz, at a certain intensity, e.g., an intensity selected from a range from about 1 W/cm$^2$ to about 50 W/cm$^2$, while the surfaces of the zirconia crown(s) 703 are etched in the etching or surface treatment solution 725. Also, while the ultrasonic impact treatment during the etching process may shorten the etching process time, but it is not necessary to use the ultrasonic impact treatment to obtain desired surface treatment results on the zirconia based crowns. Further, it is noted that ultrasonic impact treatment may produce toxic or hazardous fumes when the ultrasonic impact treatment is applied to the zirconia based crowns in the etching or surface treatment solution. For the ultrasonic impact treatment, various ultrasonic cleaning devices for dental uses may be used.

Having discussed various aspects of a system or apparatus for treating surfaces of zirconia based crowns at a high level, an example of a surface treatment process using an etching or surface treatment solution in accordance with aspects of the present disclosure is described in detail below.

By way of example, an etching or surface treatment solution may be prepared in accordance with an aspect of the present disclosure. The etching or surface treatment solution may be prepared by mixing about 70% nitric acid solution with about 48% hydrofluoric acid solution to obtain a 1-to-1 volume ratio and adding hydrogen peroxide, e.g., about 10% by weight of the surface treatment solution. In an aspect of the present disclosure, this particular composition of the etching solution facilitates the etching process, shortening a time for the etching and resulting in much better surface characteristics (e.g., more interlocking or rough characteristics) of zirconia based crowns over the existing technology and methodologies.

Figure 8:
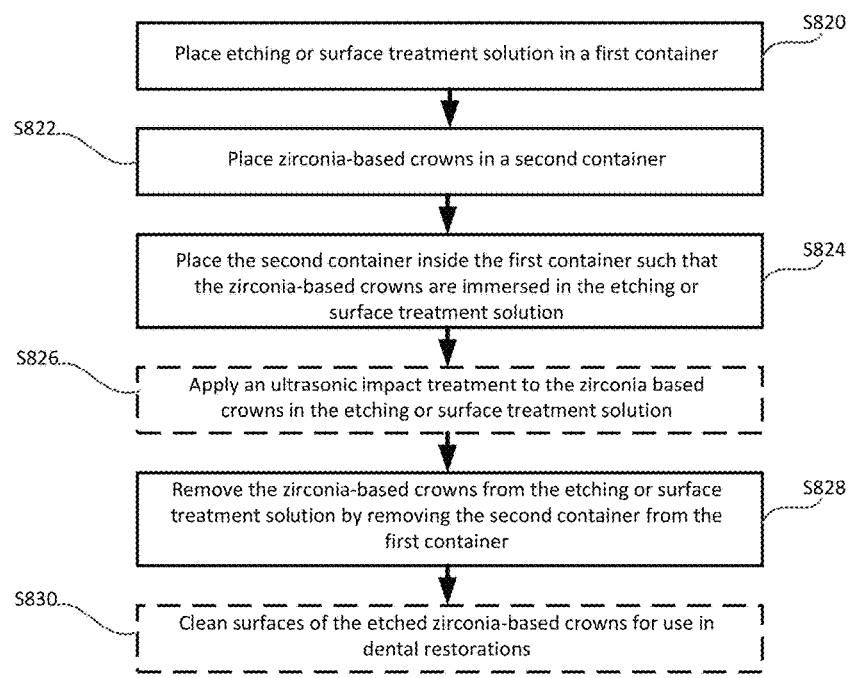
FIG. 8 illustrates an example of a flowchart for a surface treatment process in accordance with an aspect of the present disclosure.

FIG. 8 illustrates an example flowchart of an etching process. In accordance with an aspect of the present disclosure, an etching solution including at least nitric acid ($HNO_3$), hydrofluoric acid (HF) and hydrogen peroxide ($H_2O_2$) is prepared and placed into a first container such as 710, at S820. Zirconia based crowns such as 703, of which surfaces are to be etched, are placed inside a second container such as 720, at S822. The second container 720 may be a mesh type container as shown in FIGS. 5A and 5B, or alternatively, a second container 420 as shown in FIGS. 6A and 6B. In the example, at S824, the second container 720 with the zirconia based crowns 703 is placed into the first container 710 which contains the etching solution in accordance with an aspect of the present disclosure. The zirconia based crowns 703 are immersed completely in the etching or surface treatment solution flowed into the second container through a plurality of holes defined on surfaces of the second container 720 and subsequently an etching or surface treatment process takes place when the surfaces of the zirconia-based crowns come in contact with the etching solution.

Using the surface treatment process described herein, the surfaces of the zirconia based crowns 703 that are to adhere to a porcelain layer (e.g., a porcelain layer 120 shown in FIG. 2) and an abutment tooth (e.g., a tooth 100 as shown in FIG. 2) are etched or embossed. The etching process increases the surface area of the zirconia based crown s703 and as a result the etching or surface treatment has an effect of enhancing adhesive strength of the zirconia based crowns 703 (or 110) of the etching process increases surface friction and roughness, and thus increases adhesion between the abutment tooth and zirconia based crowns and between the zirconia based crown and the porcelain layer. Hence, a dental restoration obtained in accordance with aspects of the present disclosure may be secured to a top of the abutment tooth 100, with minimal chances of movements or peeling of the dental restoration.

Further, while the surfaces of the zirconia-based crowns are being etched or treated in the etching or surface treatment solution, optionally, at S826, an ultrasonic impact treatment using an ultrasonic signal at a certain intensity may be applied for a predetermined amount of time to the zirconia-based crowns in the etching or surface treatment solution. By way of example, the surface treatment of the zirconia-based crowns may be performed for up to about 120 minutes for various desired adhesive strength levels as shown in Table 1 below. As noted above, the ultrasonic impact treatment applied during the surface treatment process may facilitate a total amount of time for treating the surfaces of the zirconia based crowns to a desired level of surface characteristics and/or strength.

In an aspect of the present disclosure, for best results (e.g., surface characteristics and etching time), the ultrasonic impact treatment using an ultrasonic signal having a frequency selected from a range, e.g., about 20 kHz to about 60 kHz, preferably about 30 kHz to 50 kHz, at an intensity level selected from a range, e.g., from about 0.1 W/cm$^2$ to about 10 W/cm$^2$, preferably about 0.2 W/cm$^2$ to 1 W/cm$^2$, may be used in conjunction with the surface treatment of the zirconia-based crowns in the etching or surface treatment solution, in accordance with an aspect of the present disclosure. Alternatively, the ultrasonic impact treatment may also be carried out separately after treating surfaces of the zirconia based crowns in the etching or surface treatment solution.

After the etching of the surfaces of the zirconia based crowns 703, at S828, the zirconia based crowns 703 is removed from the etching or surface treatment solution 725 by removing the second container 720 from the first container 710. Subsequently, the zirconia based crowns 703 (the etched zirconia based crowns) are then removed from the second contained 720 for optical surface cleaning. For example, at S830, the surfaces of the etched zirconia based crowns may be optionally cleaned using various cleaning methods and/or using cleaning solution(s) such as water in one or more cleaning steps. The cleaning steps may include immersing the second container 720 with the etched zirconia based crowns 703 in a cleaning fluid or liquid to clean the surfaces of the etched zirconia based crowns 703.

After the surfaces of the zirconia based crowns 703 are treated with the surface treatment solution, one or more porcelain layers may be built up on a top of an etched zirconia based crown. In one example implementation, the porcelain layers may be built up using a lamination technique. By way of example, porcelain powder may be mixed with water to create a slurry which can be used to coat the top surface of the zirconia crown 110, e.g. by using a brush. Alternatively, other techniques for building up porcelain layer(s) may be available and suitable for use for the present disclosure. The one or more porcelain layers may comprise feldspathic porcelain including at least feldspar, silica and/or clay. By way of example, the feldspathic porcelain may contain at least about 40-85% by weight of feldspar, about 5-30% by weight of silica and about 5-30% by weight of clay. The one or more porcelain layers may also contain one or more of limes tone, porcelain stone and/or pyrophyllite. Further, the feldspathic porcelain may contain about 0.01-25% by weight of limes tone, about 0.01-15% by weight of porcelain s tone, and about 0.01-15% by weight of pyrophyllite.

After the one or more porcelain layers are built on the top surface of zirconia based crown (e.g., 110), a composite of zirconia based crown and the porcelain build-up is baked or sintered in an oven, a sintering device, or the like. During a sintering process, by way of example, the temperature may be raised at a heating rate of 1-50° C. per minute to a desired sintering temperature (for example, 800-950° C. and preferably 850° C.) and maintaining the sintering temperature for a predetermined amount of time, e.g., between about 10 seconds and about 60 minutes. As such, the sintering process may result in a final product (or a dental restoration) which includes the zirconia based crown 110 and porcelain layer(s) 120 on the top of the zirconia based crown 110 as shown in FIG. 2.

The dental restoration is then bonded to the top of an abutment tooth 100. By way of example, a bottom surface of the zirconia based crown 110 may be bonded to the abutment tooth 100 and conform to a shape of the abutment tooth 100. In some implementations, a resin cement may also be spread over on one or both of the bottom surface of the zirconia based crown 110 and top surface of the abutment tooth 100.

Dental restorations obtained in accordance with the present disclosure have various advantages and benefits. Numerous experiments have been conducted using the dental restorations obtained in accordance with various aspects of the present disclosure, and some example results of the experiments are presented below. However, it is noted that experimental conditions and results there of are presented herein merely as examples and for illustrative purposes, and the scope of the present disclosure is not to be limited to the experimental conditions or results presented herein.

To further illustrate and to provide a better understanding of the present disclosure, another description of an example of an embodiment is described as below. A zirconia crown is prepared by milling a commercial zirconia block (ZirBlank by ACUCERA) using Computer Aided Design/Computer Aided Manufacturing (CAD/CAM) to a suitable size (e.g., 10 mm×10 mm×5 mm) and subsequently sintering the milled block as a zirconia crown. By way of example, the sintering process may be carried out at a temperature of 1600° C. for 12 hours.

The etching or surface treatment solution may be prepared, in accordance with an aspect of the present disclosure, by mixing an about 70% nitric acid solution with an about 48% hydrofluoric acid solution to obtain a 1-to-1 volume ratio and adding hydrogen peroxide, e.g., 10% by weight of the surface treatment solution.

Using devices such as the first container and the second container as shown in FIGS. 4-7, the zirconia crown is immersed in the surface treatment solution for a process of etching surfaces of the zirconia crown. Further, in conjunction with the etching process, an ultrasonic impact treatment may be applied, as shown in FIG. 7, while the zirconia crown is being etched in the surface treatment solution. A duration for the surface treatment of the zirconia crown may be varied between 0 and about 120 minutes. As noted above, the ultrasonic impact treatment is not required for obtained desired surface characteristics and boding strength of the zirconia crown, but may be used to facilitate the duration for treating the surfaces of the zirconia crown. By way of example, as noted above, for the ultrasonic impact treatment, the ultrasonic impact treatment using an ultrasonic signal having a frequency selected from a range, e.g., about 20 kHz to about 60 kHz, preferably about 30 kHz to 50 kHz, at an intensity level selected from a range, e.g., from about 0.1 W/cm$^2$ to about 10 W/cm$^2$, preferably about 0.2 W/cm$^2$ to 1 W/cm$^2$, may be used in conjunction with the surface treatment of the zirconia crown in the surface treatment solution, in accordance with an aspect of the present disclosure. Alternatively, the ultrasonic impact treatment may also be performed separately after the surface treatment of zirconia crown using the surface treatment solution.

After treating the surfaces of the zirconia crown using the surface treatment solution, porcelain layer(s) are built up on a top of the zirconia crown, resulting in a composite structure. The resulting composite structure is then sintered to prepare a dental restoration or a specimen. A sintering temperature may be raised to 850° C. at a heating rate of 50° C. per minute and then maintained at that temperature for about 1 minute. Then, the dental restoration may be subsequently left to cool. Further, the porcelain layer(s) may be built up to have a thickness of 80-100 μm and reduced to a thickness of 40-50 μm by grinding, for example, to facilitate adhesive strength testing. For example, the adhesive strength between the zirconia crown and built-up porcelain layer(s) may be measured for each dental restoration specimen using a scratch test. A pressure of 50N may be applied and the results are obtained and tabulated, as shown in Table 1 below.

TABLE 1

Adhesive Strength Measurement over Surface Treatment Durations

| Duration of Surface Treatment (in minutes) | Adhesive Strength (in MPa) |
|---|---|
| 0 | 30.2 ± 0.5 |
| 10 | 31.1 ± 0.5 |
| 30 | 33.7 ± 0.5 |
| 60 | 37.1 ± 0.5 |
| 90 | 34.3 ± 0.5 |
| 120 | 28.7 ± 0.5 |

Figure 9:
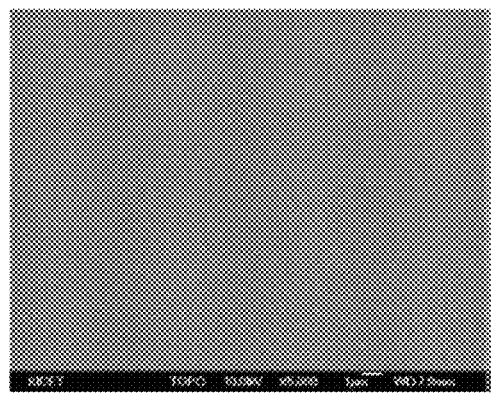
FIG. 9 shows an example image of a surface of a dental restoration without a surface treatment.
Figure 10:
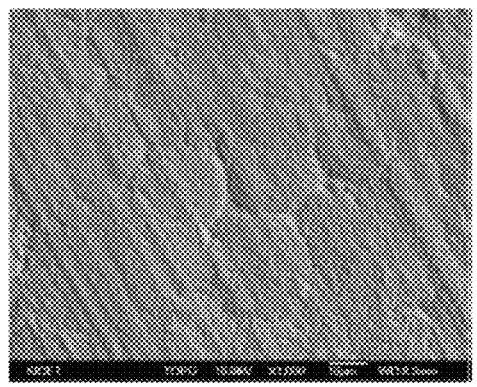
FIGS. 10-14 illustrate example images of a surface of a dental restoration in accordance with various aspects of the present disclosure.
Figure 11:
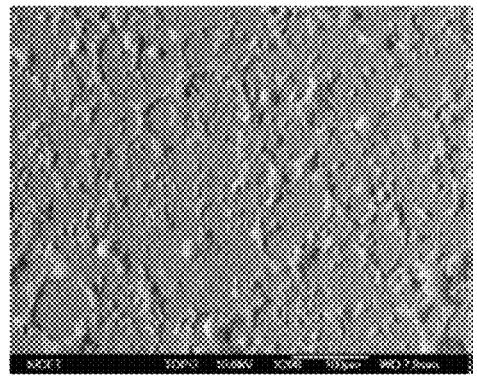
Figure 12:
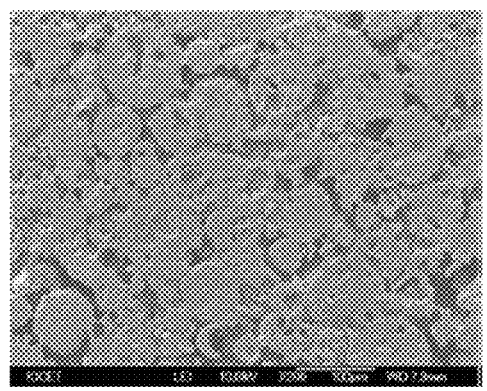
Figure 13:
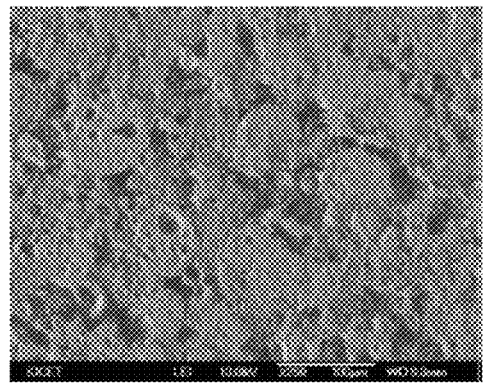
Figure 14:
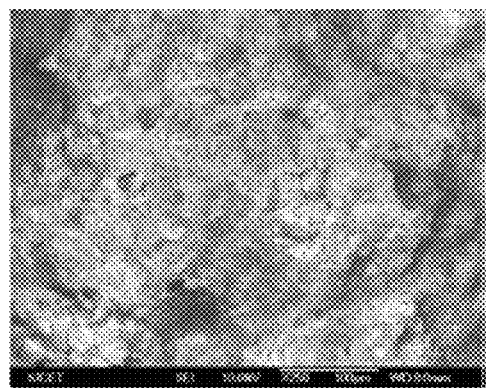

FIGS. 9-14 illustrates various example images of a surface of a dental restoration specimen, which are captured using a scanning electronic microscope. FIG. 9 shows an example image of a dental restoration specimen without the surface treatment in accordance with the present disclosure. FIG. 10 shows an example image of a dental restoration specimen with a surface treatment for about 10 minutes in accordance with an aspect of the present disclosure. FIG. 11 shows an example image of a dental restoration specimen with a surface treatment for about 30 minutes in accordance with an aspect of the present disclosure. FIG. 12 shows an example image of a dental restoration specimen with a surface treatment for about 60 minutes in accordance with an aspect of the present disclosure. FIG. 13 shows an example image of a dental restoration specimen with a surface treatment for about 90 minutes in accordance with an aspect of the present disclosure. FIG. 14 shows an example image of a dental restoration specimen with a surface treatment for about 120 minutes in accordance with an aspect of the present disclosure.

As can be seen, Table 1 and FIGS. 9 to 14 illustrate results of adhesive strength measures for various surface treatment durations. It is noted that the surface treatment for a duration between about 10 and about 90 minutes may result in an adhesive strength in excess of 31 MPa, which are significant improvements over an adhesive strength corresponding to no surface treatment of the zirconia crown. As such, the dental restorations prepared in accordance with aspects of the present disclosure provide significant enhancements and improvements over no etching or the existing technology.

Further, in an aspect of the present disclosure, the etching or surface treatment solution may be in the form of a gel type, and thus significantly reduce a level of danger working with the etching solution. In an aspect of the present disclosure, based on the components of the surface treatment solution illustrated herein, an etching gel type material containing components similar to those of the surface treatment solution may be prepared and used. For example, the etching gel may be prepared by adding colloidal silica or polymer beads type materials to the etching or surface treatment solution having a certain concentration, e.g., a concentration between 30% and 60%, as an etching agent in the gels. Further, in an aspect of the present disclosure, a viscosity enhancing agent such as carboxymethyl cellulose or the like may also be added for use in syringe type containers and use there of.

Furthermore, in an aspect of the present disclosure, the etching gel may include a color indicator such that the etching gel may be distinguished from a zirconia based crown or dental restoration. With the color indicator, the etching gel composition may be easily identified and removed completely after the etching process has been completed. Also, an amount of the color indicator added may be about 0.0001 to about 1.0 weight % of a total weight of the etching gel. Moreover, additional additives may also be added to the etching so as to make the etching gel a semi-gel type and less fluid.

Also, when an etching gel is applied to the zirconia based crowns, devices and/or equipment (e.g., first container and the second container) as shown in FIGS. 3-6 may not be needed for etching procedures. As such, use of such etching gel may increase work place safety involved in etching the zirconia based crowns. An ultrasonic impact treatment may also be applied in addition to the application of the etching gel to the zirconia crowns to facilitate the etching time and to obtain desired surface results.

As such, as described herein, the present technology provides further improved methods and apparatuses for manufacturing zirconia-based dental restorations with enhanced strength and durability, and also increase safety and efficiency in manufacturing the zirconia-based dental restorations.

While for the purpose of simplicity the methodologies are described herein as a series of steps or acts, it is to be understood that the claimed subject matter is not limited by the order of steps or acts, as some steps or acts may occur in different orders and/or concurrently with other acts from that shown and described herein. Further, not all illustrated steps or acts may be required to implement various methodologies according to the present technology disclosed herein.

The terms "first," "second," and so forth used herein may be used to describe various components, but the components are not limited by the above terms. The above terms are used only to discriminate one component from other components, without departing from the scope of the present disclosure. Also, the term "and/or" used herein includes a combination of a plurality of associated items or any item of the plurality of associated items. Further, it is noted that when it is described that an element is "coupled" or "connected" to another element, the element may be directly coupled or directly connected to the other element, or the element may be coupled or connected to the other element through a third element. A singular form may include a plural form if there is no clearly opposite meaning in the context. In the present disclosure, the term "include" or "have" used herein indicates that a feature, an operation, a component, a step, a number, a part or any combination there of described herein is present. Further, the term "include" or "have" does not exclude a possibility of presence or addition of one or more other features, operations, components, steps, numbers, parts or combinations. Furthermore, the article "a" used herein is intended to include one or more items. Moreover, no element, act, step, or instructions used in the present disclosure should be construed as critical or essential to the present disclosure unless explicitly described as such in the present disclosure.

Although the present technology has been illustrated with specific examples described herein for purposes of describing example embodiments, it is appreciated by one skilled in the relevant art that a wide variety of alternate and/or equivalent implementations may be substituted for the specific examples shown and described without departing from the scope of the present disclosure. As such, the present disclosure is intended to cover any adaptations or variations of the examples and/or embodiments shown and described herein, without departing from the spirit and the technical scope of the present disclosure.

What is claimed is:

1. A method of producing a dental restoration including a zirconia crown and one or more porcelain layers on a top surface of the zirconia crown, the method comprising:

milling a zirconia block into a shape of a zirconia crown having dimensions that are smaller than outer dimensions of an abutment tooth, thereby resulting in a molded zirconia block;

sintering the molded zirconia block to obtain the zirconia crown including a first surface and a second surface, the first surface being configured to adhere to a top of the abutment tooth and the second surface being configured to adhere to the one or more porcelain layers;

preparing and placing in a first container a surface treatment solution including at least nitric acid ($HNO_3$), hydrofluoric acid (HF) and hydrogen peroxide ($H_2O_2$);

placing the zirconia crown in a second container configured to be disposed inside the first container;

placing inside the first container the second container with the zirconia crown disposed in the second container so that the first surface and the second surface of the zirconia crown are etched in the surface treatment solution;

removing the surface treated zirconia crown from the surface treatment solution and cleaning the first and second surfaces of the zirconia crown;

building up the one or more porcelain layers on the cleaned second surface of the zirconia crown to obtain a composite; and sintering the composite to obtain the dental restoration.

2. The method of claim 1, wherein a ratio of a volume of nitric acid ($HNO_3$) in the surface treatment solution to a volume of hydrofluoric acid (HF) in the surface treatment solution is between about 1:0.1 and about 1:4, and wherein the surface treatment solution further includes hydrogen peroxide ($H_2O_2$) between about 0.1% and about 20% by weight.

3. The method of claim 1, wherein the surface treatment solution further includes acetyl chloride ($CH_3COCl$).

4. The method of claim 3, wherein the surface treatment solution further includes the acetyl chloride ($CH_3COCl$) between about 0.001% and about 10% by weight.

5. The method of claim 1, wherein the surface treatment solution further includes oxalyl chloride ($C_2O_2Cl_2$).

6. The method of claim 5, wherein the surface treatment solution further includes oxalyl chloride ($C_2O_2Cl_2$) between about 0.001% and about 10% by weight.

7. The method of claim 1, wherein treating the first and second surfaces of the zirconia crown further comprises employing an ultrasonic impact treatment using an ultrasonic signal having a frequency selected between about 20 kHz and about 60 kHz, at an intensity of between about 0.1 $W/cm^2$ and about 10 $W/cm^2$, while the first and second surfaces of the zirconia crown are being etched by the surface treatment solution.

8. The method of claim 1, wherein a time duration of treating the first and second surfaces of the zirconia crown is between about 10 minutes and about 90 minutes.

9. The method of claim 1, wherein the one or more porcelain layers comprise a feldspathic porcelain, the feldspathic porcelain containing 40%-85% by weight of feldspar, 5%-30% by weight of silica, and 5%-30% by weight of clay.

10. The method of claim 1, wherein the second container comprises a rod portion configured to be coupled to a bottom portion of the second container.

11. The method of claim 1, wherein the second container comprises an outer diameter that is smaller than an inner diameter of the first container and the second container comprises a plurality of holes on at least one of a bottom of the second container and a side wall of the second container, and the method of claim 1 further comprising:

placing the second container with the zirconia crown inside into the first container such that the zirconia crown is immersed in the surface treatment solution which flows into the second container through the plurality of holes; and removing the second container from the first container.

* * * * *